(12) United States Patent
Wang et al.

(10) Patent No.: US 8,283,310 B2
(45) Date of Patent: Oct. 9, 2012

(54) HEPATITIS C VIRUS INHIBITORS

(75) Inventors: Alan Xiangdong Wang, Guilford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 489 days.

(21) Appl. No.: 12/635,144

(22) Filed: Dec. 10, 2009

(65) Prior Publication Data

US 2010/0150866 A1   Jun. 17, 2010

Related U.S. Application Data

(60) Provisional application No. 61/122,487, filed on Dec. 15, 2008.

(51) Int. Cl.
*A61K 38/00* (2006.01)

(52) U.S. Cl. ........................................................ 514/3.7

(58) Field of Classification Search .................. None
See application file for complete search history.

(56) References Cited

U.S. PATENT DOCUMENTS

| | | | |
|---|---|---|---|
| 5,223,432 A | 6/1993 | Wirz et al. |
| 7,449,479 B2 | 11/2008 | Wang et al. |
| 7,582,605 B2 | 9/2009 | Moore et al. |
| 7,601,709 B2 | 10/2009 | Miao et al. |
| 7,605,126 B2 | 10/2009 | Niu et al. |
| 7,635,683 B2 | 12/2009 | Gai et al. |
| 2005/0209135 A1 | 9/2005 | Busacca et al. |
| 2006/0199773 A1 | 9/2006 | Sausker et al. |
| 2006/0257980 A1 | 11/2006 | Li |
| 2007/0078081 A1 | 4/2007 | Casarez et al. |
| 2008/0181868 A1 | 7/2008 | Sun et al. |
| 2008/0279821 A1 | 11/2008 | Niu et al. |
| 2009/0274656 A1 | 11/2009 | Wang et al. |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |

(Continued)

OTHER PUBLICATIONS

U.S. Appl. No. 12/628,248, filed Dec. 1, 2009, Hiebert et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).
Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

(Continued)

*Primary Examiner* — Cecilia J Tsang
*Assistant Examiner* — Thomas Heard
(74) *Attorney, Agent, or Firm* — Pamela A. Mingo

(57) ABSTRACT

Hepatitis C virus inhibitors having the general formula

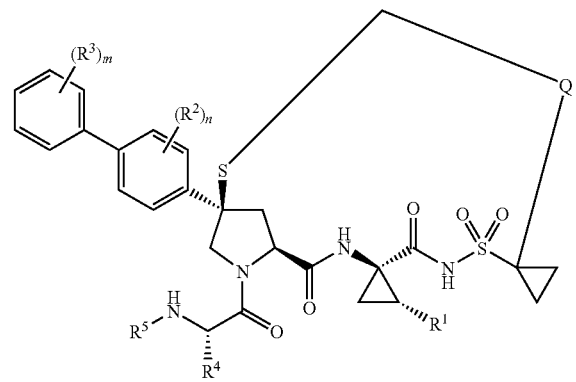

are disclosed. Compositions comprising the compounds and methods for using the compounds to inhibit HCV are also disclosed.

20 Claims, No Drawings

FOREIGN PATENT DOCUMENTS

| | | |
|---|---|---|
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005690 | 1/2009 |
| WO | WO 2009/010804 | 1/2009 |
| WO | WO 2009/014730 | 1/2009 |
| WO | WO 2009/082701 | 7/2009 |
| WO | WO 2009/085659 | 7/2009 |
| WO | WO 2009/129109 | 10/2009 |
| WO | WO 2009/140475 | 11/2009 |
| WO | WO 2009/140500 | 11/2009 |
| WO | WO 2009/142842 | 11/2009 |
| WO | WO 2009/146347 | 12/2009 |
| WO | WO 2009/148923 | 12/2009 |
| WO | WO 2009146347 | * 12/2009 |
| WO | WO 2010/030359 | 3/2010 |
| WO | WO 2010/031829 | 3/2010 |
| WO | WO 2010/031832 | 3/2010 |
| WO | WO 2010/036551 | 4/2010 |
| WO | WO 2010/036871 | 4/2010 |
| WO | WO 2010/036896 | 4/2010 |

OTHER PUBLICATIONS

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

* cited by examiner

HEPATITIS C VIRUS INHIBITORS

CROSS-REFERENCE TO RELATED APPLICATIONS

This application claims the benefit of U.S. Provisional Application Ser. No. 61/122,487 filed Dec. 15, 2008.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

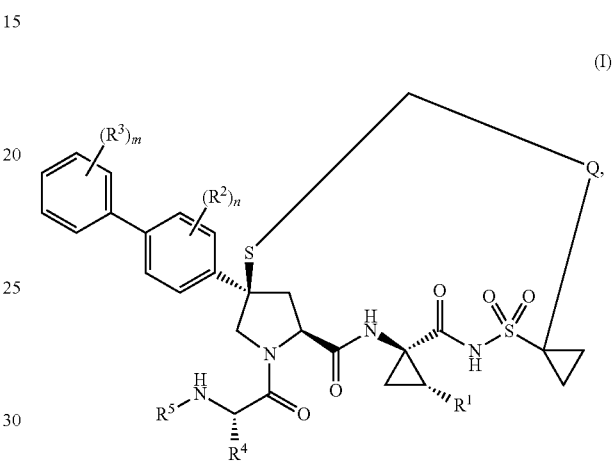

or a pharmaceutically acceptable salt thereof, wherein n and m are each independently 0, 1, 2, or 3;

$R^1$ is selected from hydrogen, alkenyl, alkyl, and cycloalkyl, wherein the alkenyl, the alkyl, and the cycloalkyl are each optionally substituted with one, two, three, or four halo groups;

each $R^2$ and $R^3$ are independently selected from alkoxy, alkyl, cyano, dialkylamino, halo, haloalkoxy, haloalkyl, and hydroxy;

$R^4$ is selected from hydrogen, alkenyl, alkyl, aryl, arylalkyl, cycloalkyl, (cycloalkyl)alkyl, heterocyclyl, and heterocyclylalkyl; wherein the alkyl and cycloalkyl are each optionally substituted with one group selected from alkoxy, haloalkoxy, halo, haloalkyl, cyano, and dialkylamino;

$R^5$ is selected from hydrogen, alkoxycarbonyl, alkyl, alkylcarbonyl, alkylsulfonyl, haloalkoxycarbonyl, haloalkyl, haloalkylcarbonyl, $(NR^aR^b)$carbonyl, and $(NR^aR^b)$sulfonyl, wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl; and Q is a $C_6$-$C_9$ saturated or unsaturated carbon chain.

In a first embodiment of the first aspect the present disclosure provides a compound of formula (I), or a pharmaceutically acceptable salt thereof, wherein $R^4$ is alkyl. In a second embodiment of the first aspect the present disclosure provides a compound of formula (I), or a pharmaceutically acceptable salt thereof, wherein $R^5$ is alkoxycarbonyl. In a third embodiment of the first aspect the present disclosure provides a compound of formula (I), or a pharmaceutically acceptable salt thereof, wherein n and m are each 0. In a fourth embodiment of the first aspect the present disclosure provides a compound of formula (I), or a pharmaceutically acceptable salt thereof, wherein $R^3$ is alkoxy. In a fifth embodiment of the first aspect the present disclosure provides a compound of formula (I), or a pharmaceutically acceptable salt thereof, wherein R¹ is alkyl substituted with two halo groups.

In a sixth embodiment of the first aspect the present disclosure provides a compound of formula (I), or a pharmaceutically acceptable salt thereof; wherein n and m are each 0;
R¹ is alkyl substituted with two halo groups;
R⁴ is alkyl;
R⁵ is alkoxycarbonyl; and
Q is a $C_7$-$C_8$ unsaturated chain.

In a second aspect the present disclosure provides a composition comprising the compound of Formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastiod interferon tau.

In a fourth embodiment of the second aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiquimod, ribavirin, an inosine 5'-monophospate dehydrogenase inhibitor, amantadine, and rimantadine.

In a fifth embodiment of the second aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a composition comprising a compound of Formula (I), or a pharmaceutically acceptable salt thereof, one, two, three, four, or five additional compounds having anti-HCV activity, and a pharmaceutically acceptable carrier. In a first embodiment of the third aspect the composition comprises three or four additional compounds having anti-HCV activity. In a second embodiment of the third aspect the composition comprises one or two additional compounds having anti-HCV activity.

In a fourth aspect the present disclosure provides a method of treating an HCV infection in a patient, comprising administering to the patient a therapeutically effective amount of Formula (I), or a pharmaceutically acceptable salt thereof. In a first embodiment of the fourth aspect the method further comprises administering at least one additional compound having anti-HCV activity prior to, after, or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastiod interferon tau.

In a fourth embodiment of the fourth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiquimod, ribavirin, an inosine 5'-monophospate dehydrogenase inhibitor, amantadine, and rimantadine.

In a fifth embodiment of the fourth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NSSA protein, and IMPDH for the treatment of an HCV infection.

In a fifth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the fifth aspect the method comprises administering three or four additional compounds having anti-HCV activity. In a second embodiment of the fifth aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^2$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a straight or branched chain group of two to ten carbon atoms containing at least one carbon-carbon double bond.

The term "alkoxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indenyl, indenyl, naphthyl, phenyl, and tetrahydronaphthyl.

The term "arylalkyl," as used herein, refers to an alkyl group substituted with one, two, or three aryl groups.

The term "cyano," as used herein, refers to —CN.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "(cycloalkyl)alkyl," as used herein, refers to an alkyl group substituted with one, two, or three cycloalkyl groups.

The term "dialkylamino," as used herein, refers to —NR$^p$R$^q$, wherein R$^p$ and R$^q$ are alkyl groups. The alkyl groups may be the same or different.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a five-, six-, or seven-membered ring containing one, two, three, or four heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to an alkyl group substituted with one, two, or three heterocyclyl groups.

The term "hydroxy," as used herein, refers to —OH.

The term "—NR$^a$R$^b$," as used herein, refers to two groups, R$^a$ and R$^b$, which are attached to the parent molecular moiety through a nitrogen atom. R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl.

The term "(NR$^a$R$^b$)carbonyl," as used herein, refers to an —NR$^a$R$^b$ group attached to the parent molecular moiety through a carbonyl group.

The term "(NR$^a$R$^b$)sulfonyl," as used herein, refers to an —NR$^a$R$^b$ group attached to the parent molecular moiety through a sulfonyl group.

The term "sulfonyl," as used herein, refers to —SO$_2$.

The compounds of the present disclosure can exist as pharmaceutically acceptable salts. The Wan "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18th ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "sulfonyl," as used herein, refers to —SO$_2$—.

The term "sulfonyl," as used herein, refers to —S(O)—.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

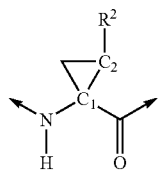

P1 wherein $C_1$ and $C_2$ each represent an asymmetric carbon atom at positions 1 and 2 of the cyclopropyl ring.

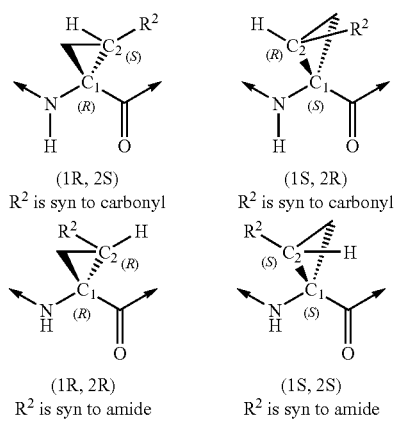

(1R, 2S)
R² is syn to carbonyl (1S, 2R)
R² is syn to carbonyl (1R, 2R)
R² is syn to amide (1S, 2S)
R² is syn to amide It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular; intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |

TABLE 1-continued

| Brand Name | Physiological Class | Type of Inhibitor or Target | Source Company |
|---|---|---|---|
| Telaprevir (VX-950, LY-570310) | Antiviral | NS3 serine protease inhibitor | Vertex Pharmaceuticals Inc., Cambridge, MA/ Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |

TABLE 1-continued

| Brand Name | Physiological Class | Type of Inhibitor or Target | Source Company |
|---|---|---|---|
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | Glaxo SmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| MK 78009 | Antiviral | serine protease inhibitor | Merck |
| TMC-435350 | Antiviral | serine protease inhibitor | Tibotec |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: DCM for dichloromethane; min for minutes; h for hours; EtOAc for ethyl acetate; HATU for O-(7-azabenzotriazol-1-yl)-N,N,N',N'-tetramethyluronium phosphate; DMSO for dimethylsulfoxide; THF for tetrahydrofuran; MeOH for methanol; BOC$_2$O for di-tert-butyldicarbonate; DMAP for 4-(N,N-dimethylamino)pyridine; TLC for thin layer chromatography; sat. for saturated; r.t./rt/RT for room temperature or retention time (context will dictate); diethylaminosulfur trifluoride; CD1 for 1,1'-carbonyldiimidazole; and DBU for 1,8-diazabicyclo-(5.4.0)undec-7-ene.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

EXAMPLE 1

Compound 1

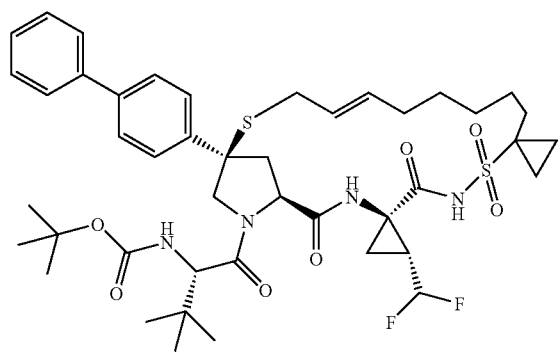

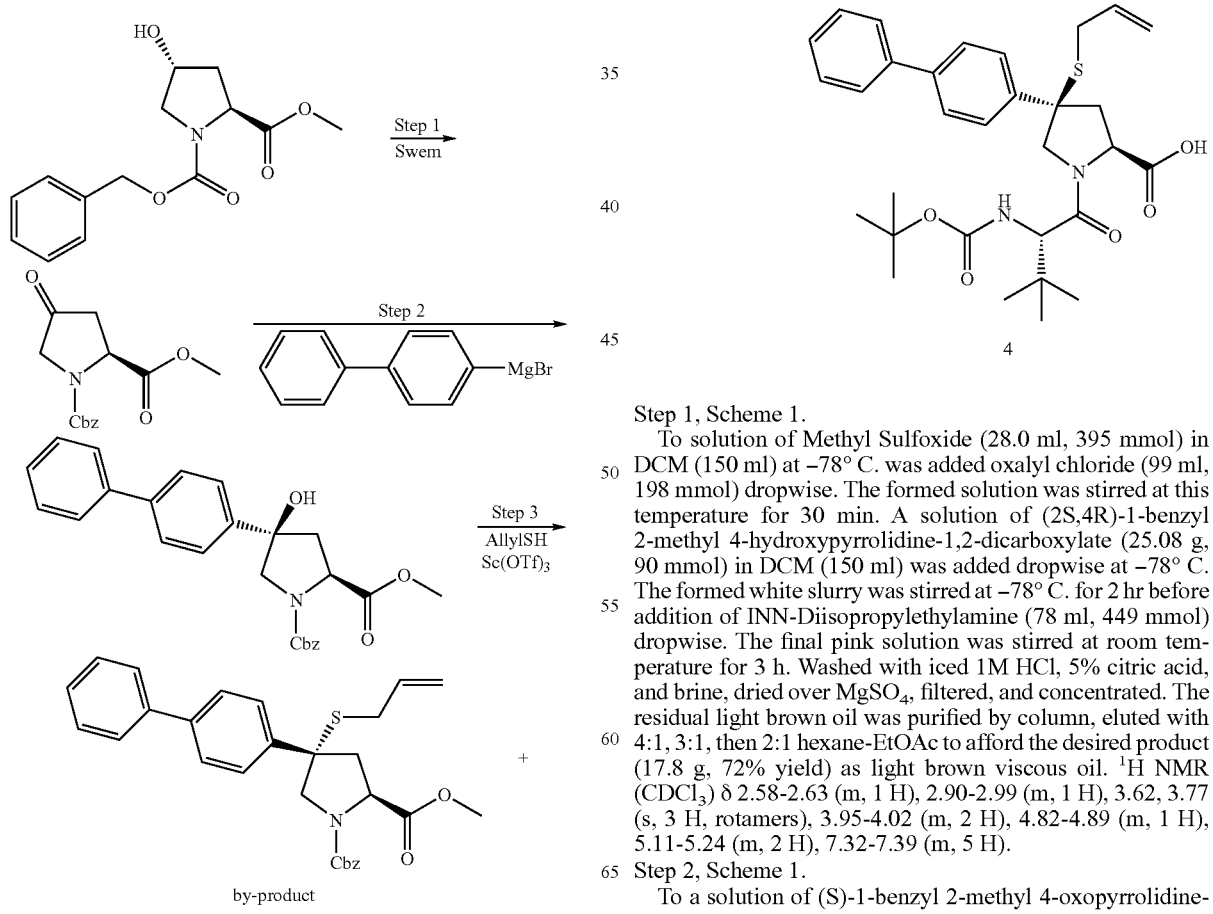

Scheme 1

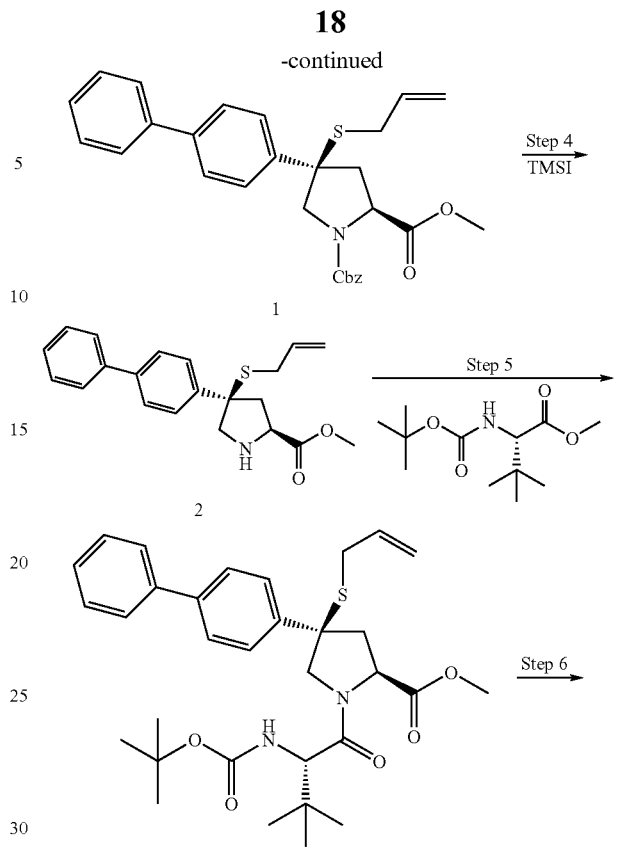

Step 1, Scheme 1.

To solution of Methyl Sulfoxide (28.0 ml, 395 mmol) in DCM (150 ml) at −78° C. was added oxalyl chloride (99 ml, 198 mmol) dropwise. The formed solution was stirred at this temperature for 30 min. A solution of (2S,4R)-1-benzyl 2-methyl 4-hydroxypyrrolidine-1,2-dicarboxylate (25.08 g, 90 mmol) in DCM (150 ml) was added dropwise at −78° C. The formed white slurry was stirred at −78° C. for 2 hr before addition of INN-Diisopropylethylamine (78 ml, 449 mmol) dropwise. The final pink solution was stirred at room temperature for 3 h. Washed with iced 1M HCl, 5% citric acid, and brine, dried over MgSO$_4$, filtered, and concentrated. The residual light brown oil was purified by column, eluted with 4:1, 3:1, then 2:1 hexane-EtOAc to afford the desired product (17.8 g, 72% yield) as light brown viscous oil. $^1$H NMR (CDCl$_3$) δ 2.58-2.63 (m, 1 H), 2.90-2.99 (m, 1 H), 3.62, 3.77 (s, 3 H, rotamers), 3.95-4.02 (m, 2 H), 4.82-4.89 (m, 1 H), 5.11-5.24 (m, 2 H), 7.32-7.39 (m, 5 H).

Step 2, Scheme 1.

To a solution of (S)-1-benzyl 2-methyl 4-oxopyrrolidine-1,2-dicarboxylate (1324 g, 47.8 mmol) in Toluene (400 mL)

at 0° C. was added biphenyl-4-ylmagnesium bromide (124 mL, 62.1 mmol) dropwise. The formed light yellow solution was stirred at this temperature for 1 h. Quenched with $NH_4Cl$, separated the organic layer. The ageous was extracted with EtOAc. Washed the combined organic layers with brine, dried over $MgSO_4$, filtered, and concentrated. The residue was purified by passing through silica gel plug, eluted with 4:1, 3:1 then 2:1, and finally 3:2 hexane-EtOAc to provide 10.50 g white solid, which was recrystallized from EtOAc-Hexane (50 ml-150 ml) to afford 7.50 g of the desired product as a small pink needle. The mother liquor was concentrated and purified by Biotage column, eluted with 5%-50% EtOAc-hexane to yield additional 1.89 g of the desired product. $^1$H NMR (CDCl$_3$) δ 2.39-2.45 (m, 1 H), 2.70-2.75 (m, 1 H), 3.66, 3.86 (s, 3 H, rotamers), 3.80-3.90 (m, 1 H), 4.00-4.07 (m, 1 H), 4.62 (dd, $J_{1,2}$=9.5, 28 Hz, 1 H), 5.09-5.15 (m, 1 H), 5.21-5.25 (m, 1 H), 7.31-7.38 (m, 6 H), 7.42-7.45 (m, 2 H), 7.54-7.59 (m, 6 H); LC-MS (retention time: 2.77 min, Method A), MS m/z 414 ($M^+$-$H_2O$), 370 ($M^+$-$H_2O$—$CO_2$).

Step 3, Scheme 1.

To a clear solution of (2S,4R)-1-benzyl 2-methyl 4-(biphenyl-4-yl)-4-hydroxypyrrolidine-1,2-dicarboxylate (3236 mg, 7.5 mmol) and prop-2-ene-1-thiol (834 mg, 9.00 mmol) in Acetonitrile (40 mL) was added Scandium(III) trifluoromethanesulfonate (369 mg, 0.750 mmol) as solid by one portion at room temperature. The formed pink solution was stirred at this temperature for 20 h. Quenched with sat. ammonium chloride, extracted with EtOAc. Washed the organic with brine, dried over $MgSO_4$, filtered, and concentrated in vacuo. The residue was purified by Biotage column, eluted with 5%~50% EtOAc-Hexane to afford a mixture of the diasteromers (2.88 g, 79%) and the starting material (0.600 g, 18%). This mixture of the diasteromers was purified by Biotage column again, eluted with 2%~8% EtOAc-Toluene to afford the desired product (2S,4R)-1-benzyl 2-methyl 4-(allylthio)-4-(biphenyl-4-yl)pyrrolidine-1,2-dicarboxylate (900 mg, 1.661 mmol, 22.15% yield) as the second peak collected from the column as a viscous oil. $^1$H NMR (500 MHz, CHLOROFORM-D) δ ppm 2.59-2.76 (m, 1 H) 2.78-2.93 (m, 3 H) 3.60 (s, 1.5 H) 3.77 (s, 1.5 H) 3.92 (d, J=11.60 Hz, 1 H) 4.17-4.31 (m, 1 H) 4.34-4.49 (m, 1 H) 4.92-5.07 (m, 2 H) 5.08-5.34 (m, 2 H) 5.53-5.72 (m, 1 H) 7.23-7.41 (m, 6 H) 7.45 (t, J=7.63 Hz, 3 H) 7.48-7.67 (m, 5 H).

LC-MS (retention time: 3.32 min, Method A), MS m/z 488 (M+H).

Step 4, Scheme 1.

To an iced solution of (2S,4R)-1-benzyl 2-methyl 4-(allylthio)-4-(biphenyl-4-yl)pyrrolidine-1,2-dicarboxylate (1.85 g, 3.79 mmol) in Acetonitrile (20 mL) was added Iodotrimethylsilane (0.810 mL, 5.69 mmol). The formed light brown solution was stirred at room temperature for 2 h. Cooled with ice bath, quenched with Methyl alcohol (7.68 mL, 190 mmol). The formed light brown solution was purified by prep-HPL, and the collected fractions were evaporated on speed-vac system. The yellow residue was taken up in DCM, washed with sat. $Na_2CO_3$ and brine, dried over $MgSO_4$, filtered, and concentrated in vacuo to afford the desired product (2S,4R)-methyl 4-(allylthio)-4-(biphenyl-4-yl)pyrrolidine-2-carboxylate (664 mg, 1.878 mmol, 49.5% yield) as a viscous oil. $^1$H NMR (500 MHz, MeOD) δ ppm 2.96-3.09 (m, 3 H) 3.15 (d, J=14.34 Hz, 1 H) 3.84 (d, J=12.21 Hz, 1 H) 3.96 (s, 2.5 H) 4.00 (s, 0.5 H) 4.04 (d, J=11.90 Hz, 1 H) 4.77 (dd, J=10.07, 3.05 Hz, 1 H) 5.02 (d, J=9.77 Hz, 1 H) 5.09 (d, J=17.09 Hz, 1 H) 5.54-5.68 (m, 1 H) 7.38 (t, J=7.48 Hz, 1 H) 7.44-7.54 (m, 4 H) 7.66 (d, J=7.32 Hz, 2 H) 7.71 (d, J=8.55 Hz, 2 H).

LC-MS (retention time: 2.21 min, Method A), MS m/z 354 (M+H).

Step 5, Scheme 1.

To a slurry of (2S,4R)-methyl 4-(allylthio)-4-(biphenyl-4-yl)pyrrolidine-2-carboxylate (355 mg, 1.004 mmol), (S)-2-(tert-butoxycarbonylamino)-3,3-dimethylbutanoic acid (256 mg, 1.105 mmol), and HATU (573 mg, 1.506 mmol) in DCM (10 mL) was added N,N-Diisopropylethylamine (0.526 mL, 3.01 mmol). The formed solution was stirred at room temperature overnight. Washed with 1M HCl, 1M NaOH, and brine, dried over $MgSO_4$, filtered, and concentrated. The residue was purified by Biotage column, eluted with gradient 5%-50% Acetone-Hexane to afford the desired product (2S,4R)-methyl 4-(allylthio)-4-(biphenyl-4-yl)-1-(S)-2-(tert-butoxycarbonylamino)-3,3-dimethylbutanoyl)pyrrolidine-2-carboxylate (416 mg, 0.661 mmol, 65.8% yield) as a white foam. $^1$H NMR (400 MHz, MeOD) δppm 1.10 (s, 9 H) 1.46 (s, 9 H) 2.54 (dd, J=12.80, 7.78 Hz, 1 H) 2.86-3.02 (m, 3 H) 3.72 (s, 3 H) 3.98-4.11 (m, 1 H) 4.30 (t, J=7.65 Hz, 1 H) 4.37-4.48 (m, 1 H) 4.74-4.87 (m, 1 H) 4.94-5.12 (m, 2 H) 5.63-5.79 (m, 1 H) 7.35 (t, J=7.28 Hz, 1 H) 7.44 (t, J=7.53 Hz, 2 H) 7.57-7.71 (m, 6 H); LC-MS (retention time: 3.09 min, Method B), MS m/z 567 (M+H).

Step 6, Scheme 1.

To a solution of (2S,4R)-methyl 4-(allylthio)-4-(biphenyl-4-yl)-1-((S)-2-(tert-butoxycarbonylamino)-3,3-dimethylbutanoyl)pyrrolidine-2-carboxylate (362 mg, 0.639 mmol) in THF (5 mL) and MeOH (5.00 mL) was added pre-made solution of lithium hydroxide hydrate (80 mg, 1.916 mmol) in Water (5 mL). The resulting cloudy solution was stirred at room for 24 h. Quenched with 5% citric acid, extracted with EtOAc. The organic layer was washed with brine, dried over $MgSO_4$, filtered, and concentrated, to afford the desired product (2S,4R)-4-(allylthio)-4-(biphenyl-4-yl)-1-((S)-2-(tert-butoxycarbonylamino)-3,3-dimethylbutanoyl)pyrrolidine-2-carboxylic acid (312 mg, 0.553 mmol, 87% yield) as a white solid.

LC-MS (retention time: 2.96 min, Method B), MS m/z 553 (M+H).

Scheme 2

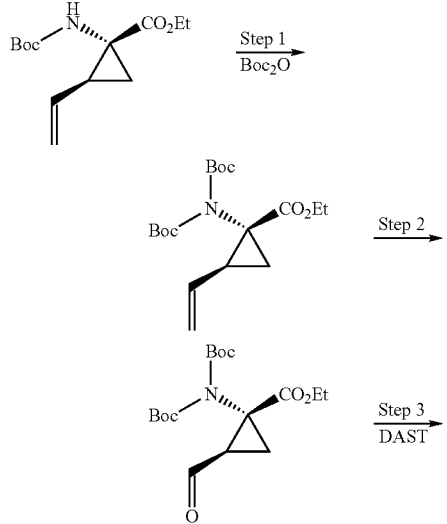

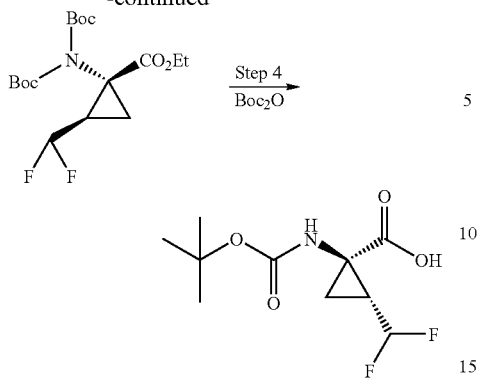

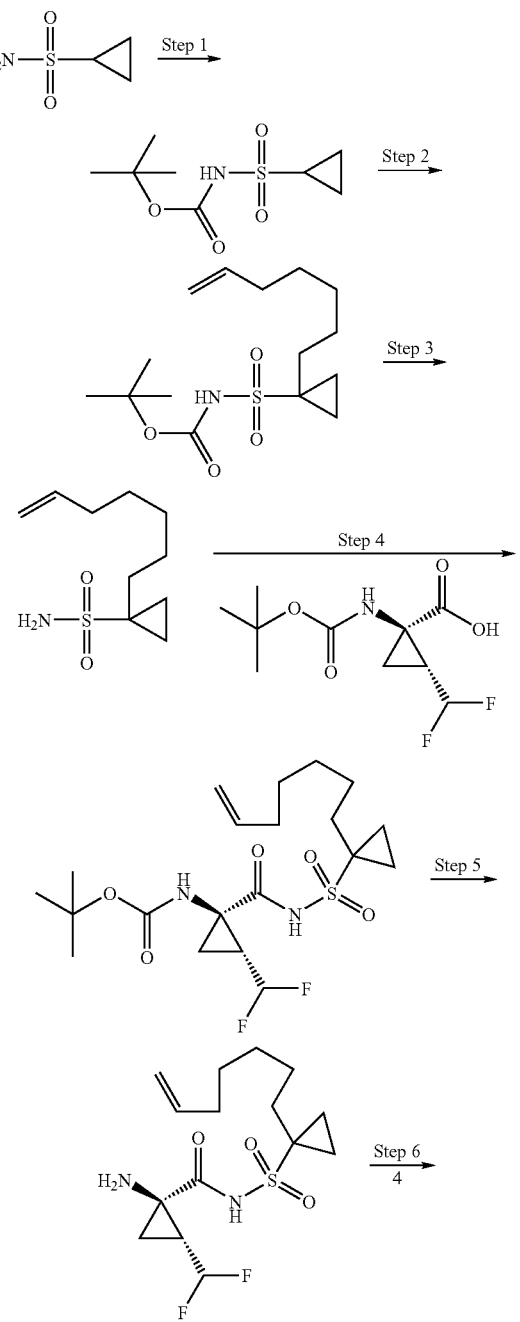

Scheme 3

Step 1, Scheme 2.

A solution of (1R,2S)-benzyl 1-(tert-butoxycarbonylamino)-2-vinylcyclopropanecarboxylate (4.82 g, 15.19 mmol), BOC$_2$O (7.05 mL, 30.4 mmol), and DMAP (0.371 g, 3.04 mmol) were heated at 45° C. and monitored by TLC. The reaction was cooled and diluted with EtOAc. This was washed with sat NaHCO$_3$ solution, then sat. NH$_4$Cl solution and then brine. The organics were dried, filtered and concentrated to give crude material. This was purified on the Biotage (5-20% EtOAc/hexanes) to give the product as a colorless oil, W=5.8 g (91%). $^1$H NMR (500 MHz, CHLOROFORM-d) δ ppm 1.24 (t, J=7.17 Hz, 3 H), 1.32-1.44 (m, 1 H), 1.45-1.67 (m, 18 H), 1.89 (dd, J=8.70, 5.95 Hz, 1 H), 2.26 (q, J=8.95 Hz, 1 H), 4.05-4.35 (m, 2 H), 5.15 (dd, J=10.22, 1.37 Hz, 1 H), 5.23-5.48 (m, 1 H), 5.87 (ddd, J=17.24, 9.61, 9.46 Hz, 1 H).

Step 2, Scheme 2,

OSMIUM TETROXIDE (1.891 mL, 0.309 mmol) was added to a solution of (1R,2S)-ethyl 1-(bis(tert-butoxycarbonyl)amino)-2-vinylcyclopropanecarboxylate (11 g, 30.9 mmol) in t-butanol (500 mL) and Tetrahydrofuran (50.0 mL) at 0° C. To this was added a solution of SODIUM PERIODATE (16.55 g, 77 mmol) in Water (50 mL). The reaction turned to a thick slurry of white precipitate. After 15 min, the ice bath was removed and the reaction allowed to warm up to r.t. overnight. The reaction was filtered through celite. Washed the cake with EtOAc. The filtrate was concentrated in vacuo. The residue was taken up in EtOAc and washed with brine. The organics were dried, filtered and evaporated to give crude material. The crude was purified on the Biotage (15-20% EtOAc/hexanes) to give the product as a colorless oil W-9 g (81%). $^1$H NMR (300 MHz, CHLOROFORM-d) δ ppm 1.27 (t, J=7.14 Hz, 3 H) 1.50 (s, 18 H) 1.78 (dd, J=9.51, 6.22 Hz, 1 H) 2.30 (td, J=9.06, 5.67 Hz, 1 H) 2.48 (dd, J=8.42, 6.22 Hz, 1 H) 4.16-4.33 (m, 2 H) 9.47 (d, J=5.86 Hz, 1 H); LC-MS: 412 (MW+32+22+1).

Step 3, Scheme 2.

DAST (3.14 mL, 23.78 mmol) was added to a solution of (1R,2R)-ethyl 1-(bis(tert-butoxycarbonyl)amino)-2-formylcyclopropanecarboxylate (1.7 g, 4.76 mmol) in Dichloromethane (50 mL) at 0° C. and stirred for 3 h at 0° C. The reaction was quenched by dropwise addition to a cold sat. NaHCO$_3$ solution. The organics were washed with sat. sodium chloride, dried (MgSO$_4$), filtered and concentrated to give crude material. The crude material was purified by flash chromatography on the Biotage (10% EtOAc in hexanes) to give the pure product as a colorless oil, W=600 mg (33.2%). $^1$H NMR (300 MHz, CHLOROFORM-d) δ ppm 1.14-1.29 (m, 1 H) 1.21 (t, J=7.14 Hz, 3 H) 1.33-1.52 (m, 18 H) 1.81-1.94 (m, 1 H) 1.98-2.18 (m, 1 H) 4.16 (q, J=6.95 Hz, 2 H) 5.65-6.13 (m, J=55.62, 55.62, 7.32, 7.32, 7.32 Hz, 1 H).

Step 4, Scheme 2.

A mixture of (1R,2R)-ethyl 1-(bis(tert-butoxycarbonyl)amino)-2-(difluoromethyl)cyclopropanecarboxylate (540 mg, 1.423 mmol) in Tetrahydrofuran (7 mL) and MeOH (7.00 mL) was added 2M LiOH (3.56 mL, 7.12 mmol) in water and stirred at rt over the weekend. It was then extracted with ether, the aqueous layer was acidified with 1N HCl until pH=3. It was then extracted with ethyl acetate, dried over MgSO$_4$, filtered and concentrated to yield W=340 mg (95%) off-white solid. $^1$HNMR (500 MHz, MeOD) δ ppm 1.39-1.54 (m, 10 H,) 1.64-1.87 (m, 1 H), 1.88-2.11 (m, 1 H,) 5.91 (t, J=55.85 Hz, 1 H).

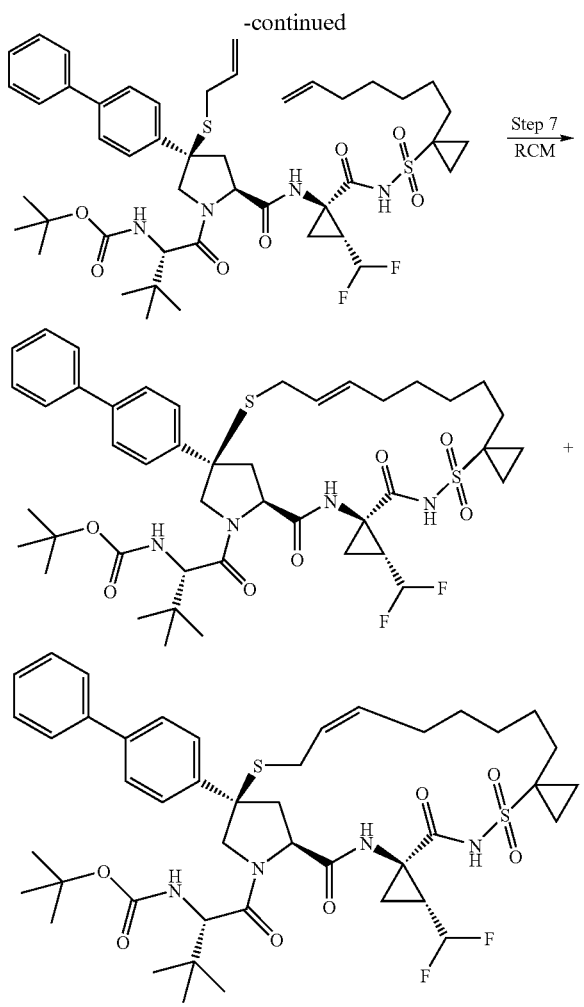

Step 1, Scheme 3.

To an iced slurry of cyclopropanesulfonamide (1.21 g, 9.99 mmol), Triethylamine (2.95 mL, 20.97 mmol), and 4-Dimethylaminopyridine (0.061 g, 0.499 mmol) in CH$_2$Cl$_2$ (50 mL) was added solution of Di-tert-butyl dicarbonate (2.423 mL, 10.99 mmol) in DCM (10 mL) dropwise. The formed solution was stirred at room temperature overnight, Removed the solvent in vacuo. The residual oil was taken up in EtOAc and washed with 1M HCl and brine. Dried over MgSO$_4$, filtered, and concentrated. The residue was purified by Biotage column, eluted with gradient 5%~50% acetone-hexane to yield the desired produce tert-butyl cyclopropylsulfonylcarbamate (2.17 g, 9.61 mmol, 96% yield) as a viscous oil, which solidified upon standing on bench. $^1$H NMR (400 MHz, CDCl$_3$) δppm 1.11-1.13 (m, 2 H) 1.37-1.39 9m, 2 H) 1.53 (s, 9 H), 2.89-2.92 (m, 1 H) 7.00-7.05 (b, NH).

Step 2, Scheme 3.

To a solution of tert-butyl cyclopropylsulfonylcarbamate (885 mg, 4 mmol) in THF (20 mL) at −78° C. was added n-Butyllithium (3.36 mL, 8.40 mmol) (2.5 M in hexanes) dropwise. The formed solution was warmed up to r.t. and stirred for 1.5 h. Cooled this light yellow solution back to −78° C. 7-Bromo-1-heptene (1.219 mL, 8.00 mmol) was added dropwise. The final solution was allowed to warm up to r.t. over the period of 16 h. Quenched with sat. NH4Cl, extracted with EtOAc. The organic layer was washed with brine, dried over MgSO$_4$, filtered, and concentrated. The residue was purified by Biotage column, eluted with gradient 5%~40% EtOAc-Hexane to afford the desired product tert-butyl 1-(hept-6-enyl)cyclopropylsulfonylcarbamate (625 mg, 1.772 mmol, 44.3% yield) as a viscous oil, which solidified upon standing on bench. $^1$H NMR (400 MHz, CHLOROFORM-D) δppm 0.88-1.02 (m, 2 H) 1.26-1.49 (m, 6 H) 1.53 (s, 9 H) 1.60-1.71 (m, 2 H) 1.82-1.94 (m, 2 H) 2.06 (q, J=6.94 Hz, 2 H) 4.81-5.08 (m, 2 H) 5.68-5.88 (m, 1 H) 6.88 (b, NH). LC-MS (retention time: 2.76 min, Method A), MS m/z 218 (M+H-Boc).

Step 3, Scheme 3.

4.0M HCl in dioxane (4.285 mL, 17.14 mmol) was added to tert-butyl 1-(hept-6-enyl)cyclopropylsulfonylcarbamate (544 mg, 1.714 mmol) and stirred at r.t. for 3 h. Poured into water, extracted with EtOAc. The organic layer was washed with brine, dried over MgSO$_4$, filtered, concentrated in vacuo. The residue was purified by Biotage column, eluted with gradient 5%~60% EtOAc-Hexane to afford the desired product 1-(hept-6-enyl)cyclopropane-1-sulfonamide (350 mg, 1.578 mmol, 92% yield) as a white solid. $^1$H NMR (400 MHz, CHLOROFORM-D) δppm 0.82-0.94 (m, 2 H) 1.28-1.53 (m, 8 H) 1.84-1.97 (m, 2 H) 2.06 (q, J=6.94 Hz, 2 H) 4.49 (b, NH$_2$) 4.89-5.07 (m, 2 H) 5.70-5.90 (m, 1 H).

Step 4, Scheme 3.

To a solution of (1R,2R)-1-(tert-butoxycarbonylamino)-2-(difluoromethyl)cyclopropanecarboxylic acid (100 mg, 0.398 mmol) in Tetrahydrofuran (4 mL) was added CDT (84 mg, 0.517 mmol) and the formed solution was stirred at r.t. for 3 h. 1-(hept-6-enyl)cyclopropane-1-sulfonamide (104 mg, 0.478 mmol) and DBU (0.120 mL, 0.796 mmol) were added and the reaction continued at r.t. overnight. The reaction was diluted with EtOAc. Washed with 5% citric acid, brine, dried over MgSO$_4$, filtered and concentrated. The residue was purified by Biotage column, eluted with gradient 5%~70% EtOAc-Hexane to afford the desire produce tert-butyl (1R, 2R)-2-(difluoromethyl)-1-(1-(hept-6-enyl)cyclopropylsulfonylcarbamoyl)cyclopropylcarbamate (45 mg, 0.100 mmol, 25.09% yield). $^1$H NMR (400 MHz, CHLOROFORM-D) δppm 0.95 (s, 2 H) 1.28-1.36 (m, 2 H) 1.36-1.47 (m, 6 H) 1.52 (s, 9 H) 1.58-1.67 (m, 2 H) 1.72 (d, J=10.54 Hz, 1 H) 1.78-1.95 (m, 2 H) 1.97-2.12 (m, 3 H) 4.88-5.05 (m, 2 H) 5.23 (b, NH) 5.65-5.92 (m, 2 H) 9.20 (b, NH).

Step 5, Scheme 3.

4.0M HCl in dioxane (500 μL, 2 mmol) was added to tert-butyl (1R,2R)-2-(difluoromethyl)-1-(1-(hept-6-enyl)cyclopropylsulfonylcarbamoyl)cyclopropylcarbamate (45 mg, 0.100 mmol) and stirred at r.t. overnight. Removed the solvent in vacuo. The formed product was used as crude for the next coupling reaction. $^1$H NMR (400 MHz, MeOD) δppm 0.89-1.07 (m, 2 H) 1.26-1.65 (m, 8 H) 1.72 (t, J=2.76 Hz, 1 H) 1.82-1.95 (m, 2 H) 2.06 (q, J=7.03 Hz, 2 H) 2.17-2.32 (m, 2 H) 4.89-4.95 (m, 1 H) 4.95-5.06 (m, 1 H) 5.69-6.19 (m, 2 H).

Step 6, Scheme 3.

To a slurry of (2S,4R)-4-(allylthio)-4-(biphenyl-4-yl)-1-((S)-2-(tert-butoxycarbonylamino)-3,3-dimethylbutanoyl)pyrrolidine-2-carboxylic acid (55.3 mg, 0.10 mmol), (1R, 2R)-1-amino-2-(difluoromethyl)-N-(1-(hept-6-enyl)cyclopropylsulfonyl)cyclopropanecarboxamide (38.7 mg, 0.10 mmol) and HATU (57.0 mg, 0.150 mmol) in DCM (2 mL) was added N,N-Diisopropylethylamine (0.087 mL, 0.500 mmol). The formed solution was stirred at room temperature overnight. Diluted with DCM, washed with 1M HCl and brine, dried over MgSO$_4$, filtered, and concentrated. The residue was purified by Biotage column, eluted with gradient 5%~30% Acetone-Hexane to afford the desired product tert-butyl (S)-1-((2S,4R)-4-(allylthio)-4-(biphenyl-4-yl)-2-((1R, 2R)-2-(difluoromethyl)-1-(1-(hept-6-enyl)cyclopropylsulfonylcarbamoyl)cyclopropylcarbamoyl)pyrrolidin-1-yl)-3,3-dimethyl-1-oxobutan-2-ylcarbamate (65 mg, 0.073 mmol, 73% yield) as a white foam. $^1$H NMR (400 MHz, MeOD) δppm 0.81-0.88 (m, 2 H) 1.07 (s, 9 H) 1.21-1.61 (m, 17 H) 1.64-1.80 (m, 1 H) 1.81-2.12 (m, 6 H) 2.37 (t, J=11.42 Hz, 1 H) 2.91-3.05 (m, 3 H) 3.91 (dd, J=10.29, 6.53 Hz, 1 H) 3.98 (d, J=11.04 Hz, 1 H) 4.48 (d, J=9.79 Hz, 1 H) 4.86-5.13 (m, 5 H) 5.66-6.14 (m, 3 H) 7.36 (t, J=7.28 Hz, 1 H) 7.45 (t, J=7.53 Hz, 2 H) 7.52-7.76 (m, 6 H). LC-MS (retention time: 3.39 min, Method B), MS m/z 885 (M+H).

Step 7, Scheme 3.

A solution of tert-butyl (S)-1-(2S,4R)-4-(allylthio)-4-(biphenyl-4-yl)-2-((1R,2R)-2-(difluoromethyl)-1-(1-(hept-6-enyl)cyclopropylsulfonylcarbamoyl)cyclopropylcarbamoyl)pyrrolidin-1-yl)-3,3-dimethyl-1-oxobutan-2-ylcarbamate (73 mg, 0.082 mmol) in Dichloromethane (20 mL) was purged with nitrogen for 5 min. And then Hoveyda-Grubbs Catalyst 2nd Generation (62.2 mg, 0.099 mmol) was added. The resulting green solution was heated to reflux for 5 h. Removed the solvent in vacuo. The greenish residue was purified by Biotage column, eluted with gradient 5%~40% Acetone-Hexane to afford the desired product as off-white solids, (12 mg, 0.013 mmol, 15.45% yield).

$^1$H NMR (400 MHz, MeOD) δppm 0.92-1.10 (m, 1 H) 1.34-1.62 (m, 18 H) 1.64-1.83 (m, 2 H) 1.93-2.11 (m, 4 H) 2.75 (dd, J=13.05, 10.54 Hz, 1 H) 2.87 (dd, J=15.31, 7.03 Hz, 1 H) 3.10-3.25 (m, 2 H) 4.02 (d, J=10.79 Hz, 1 H) 4.17 (dd, J=10.04, 6.53 Hz, 1 H) 4.26-4.38 (m, 1 H) 4.73 (d, J=10.54 Hz, 1 H) 5.53-5.69 (m, 2 H) 5.69-6.06 (m, 1 H) 6.41 (d, J=9.29 Hz, NH) 7.35 (t, J=7.28 Hz, 1 H) 7.44 (1, J=7.53 Hz, 2 H) 7.53-7.75 (m, 6 H).

LC-MS (retention time: 3.27 min, Method B), MS m/z 801 (M+H-t-Bu).

EXAMPLE 2

Compound 2

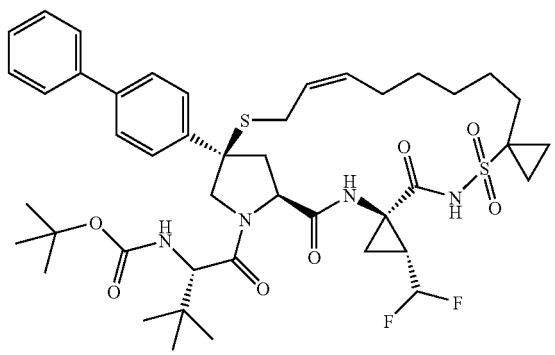

From the same reaction in Scheme 3, Step 7, the cis isomer was also separated as a white solid (3 mg, 3.15 μmol, 3.82% yield).

$^1$H NMR (400 MHz, MeOD) δ ppm 0.88-0.99 (m, 2 H) 0.98-1.13 (m, 9 H) 1.38 (s, 9 H) 1.42-1.67 (m, 11 H) 1.68-1.83 (m, 2 H) 1.90-2.04 (m, 1 H) 2.12-2.30 (m, 1 H) 2.79 (dd, J=13.18, 8.91 Hz, 1 H) 2.96-3.07 (m, 1 H) 3.13-3.25 (m, 11 H) 4.15 (d, J=11.04 Hz, 1 H) 4.26 (1, J=7.91 Hz, 1 H) 4.33 (t, J=10.29 Hz, 1 H) 4.65 (d, J=10.79 Hz, 1 H) 5.30-5.43 (m, 1 H) 5.46-5.57 (m, 1 H) 5.70-6.10 (m, 1 H) 6.45 (d, J=9.54 Hz, NH) 7.34 (t, J=7.28 Hz, 1 H) 7.43 (t, J=7.53 Hz, 2 H) 7.53-7.80 (m, 6H). LC-MS (retention time: 3.27 min, Method B), MS m/z 801 (M+H-t-Bu).

LC/MS conditions for Method A.
Start % B=0
Final % B-100
Gradient Time=3 min
Stop Time=4 min
Flow Rate=4 ml/min
Wavelength=220
Solvent A=90% Water-10% Methanol-0.1% TFA
Solvent B=10% Water-90% Methanol-0.1% TFA
Column 3=(3) PHENOMENEX-LUNA 4.6×50 mm S10

LC/MS conditions for Method B.
Start % B=30
Final % B=100
Gradient Time=3 min
Stop Time=4 min
Flow Rate=4 ml/min
Wavelength=220
Solvent A=90% Water-10% Methanol-0.1% TFA
Solvent B=10% Water-90% Methanol-0.1% TFA
Column 3=(3) PHENOMENEX-LUNA 4.6×50 mm S10

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L65 strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J Proc. Natl. Acad. Sci. U.S.A.* 94(16), 8738-8743 (1997); AF054247, see Yanagi, M., St Claire; M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Bio-* chemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21 b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J. Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultracentrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol. (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 µM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, y=A+((B−A)/(1+((C/x)^D))).

Compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 µM depending on their potency. The enzyme assays were each initiated by addition of substrate to enzyme-inhibitor pre-incubated for 10 min at room temperature and hydrolysis to 15% conversion as measured on cytofluor.

The final conditions for each assay were as follows:

50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 µM LLVY-AMC and 1 nM Chymotrypsin.

50 M Tris-HCl, pH 8.0, 50 mM NaCl, 0.1 mM EDTA, 3% DMSO, 0.02% Tween-20, 5 µM succ-AAPV-AMC and 20 nM HNE or 8 nM PPE;

100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$$[1-(UV_{inh}-UV_{blank})/(UV_{etl}-UV_{blank}))]\times 100$$

A non-linear curve fit was applied to the inhibition-concentration data, and the 50% effective concentration ($IC_{50}$) was calculated by the use of Excel XLfit software.

Generation of HCV Replicons

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. The replicon construct was modified by inserting cDNA encoding a humanized form of the Renilla luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine; later numbered S2204I) was also introduced (Blight K J, Kolykhalov, A A, Rice, C M, Science 2000 290(5498):1972-1974). Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV genotype 1a replicon cell line was generated with a similar genomic map as described above for the 1b replicon cell line. An additional adaptive substitution at position 1496 (proline to leucine) was also introduced (Lemm J A, Liu M, Rose R E, Fridell R, O'Boyle Ii D R, Colonno R, Gao M. Intervirology. 2005 48(2-3):183-91). The sequence of the H77 infectious clone (see above for details) was used to generate the sub-replicon which also contained the selectable marker G418 and the Renilla luciferase gene.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, *J. Virol.* 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL).). Compounds were serially diluted 3-fold in DMSO for a twenty-point titration and subsequently transferred to sterile 384-well tissue-culture treated plates (Corning cat #3571). Cells (50 µL in DMEM containing 4% FCS) were then seeded in these plates at a density of $3.0\times10^3$ cells/well (0.5% final DMSO concentration). After 3 days incubation at 37° C., cells were analyzed for Renilla Luciferase activity using the EnduRen as substrate (Promega cat 4E6485). The EnduRen substrate was diluted in DMEM and then added to the plates to a final concentration of 7.5 µM. The plates were incubated for 2 hrs at 37° C. and then read immediately for 30 seconds on the Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). Cell-Titer Blue (3 µL) was added to each well and incubated for 8 hrs at 37° C. The fluorescence signal from each well was read, with an excitation wavelength at 525/10 nm and an emission wavelength of 598/10 nm, on the Viewlux Imager.

The percentage inhibition was calculated using the formula below:

$$\% \text{ control} = \frac{\text{average luciferase signal in experimental wells (+compound)}}{\text{average luciferase signal in } DMSO \text{ control wells (-compound)}}$$

The values were graphed and analyzed using XLfit to obtain the $EC_{50}$ value.

The compounds of the current disclosure was tested and found to have the activity as follows:

|  | IC50 (nM) | 1a/1b EC50 (nM) |
|---|---|---|
| Compound 1 | 2 | 49/21 |
| Compound 2 | 4 | 95/33 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

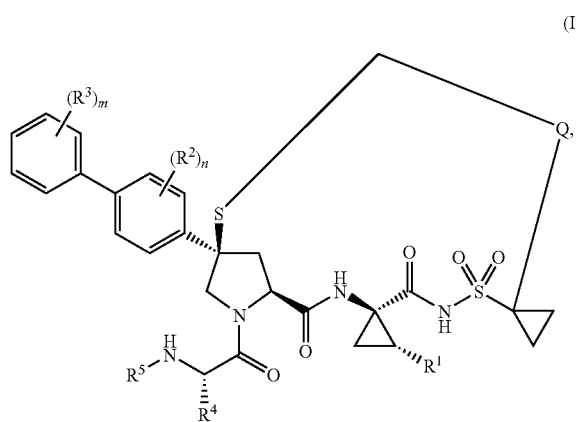

(I)

or a pharmaceutically acceptable salt thereof, wherein
n and m are each independently 0, 1, 2, or 3;
$R^1$ is selected from hydrogen, alkenyl, alkyl, and cycloalkyl, wherein the alkenyl, the alkyl, and the cycloalkyl are each optionally substituted with one, two, three, or four halo groups;
each $R^2$ and $R^3$ are independently selected from alkoxy, alkyl, cyano, dialkylamino, halo, haloalkoxy, haloalkyl, and hydroxy;
$R^4$ is selected from hydrogen, alkenyl, alkyl, aryl, arylalkyl, cycloalkyl, (cycloalkyl)alkyl, heterocyclyl, and heterocyclylalkyl; wherein the alkyl and cycloalkyl are each optionally substituted with one group selected from alkoxy, haloalkoxy, halo, haloalkyl, cyano, and dialkylamino;
$R^5$ is selected from hydrogen, alkoxycarbonyl, alkyl, alkylcarbonyl, alkylsulfonyl, haloalkoxycarbonyl, haloalkyl, haloalkylcarbonyl, $(NR^aR^b)$carbonyl, and $(NR^aR^b)$sulfonyl, wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl; and
Q is a $C_6$-$C_9$ saturated or unsaturated carbon chain.

2. A compound of claim 1, or a pharmaceutically acceptable salt thereof, wherein $R^4$ is alkyl.

3. A compound of claim 2, or a pharmaceutically acceptable salt thereof, wherein $R^5$ is alkoxycarbonyl.

4. A compound of claim 3, or a pharmaceutically acceptable salt thereof, wherein n and m are each 0.

5. A compound of claim 4, or a pharmaceutically acceptable salt thereof, wherein $R^3$ is alkoxy.

6. A compound of claim 5, or a pharmaceutically acceptable salt thereof, wherein $R^1$ is alkyl substituted with two halo groups.

7. A compound of claim 1, or a pharmaceutically acceptable salt thereof, wherein
n and m are each 0;
$R^1$ is alkyl substituted with two halo groups;
$R^4$ is alkyl;
$R^5$ is alkoxycarbonyl; and
Q is a $C_7$-$C_8$ unsaturated chain.

8. A compound selected from

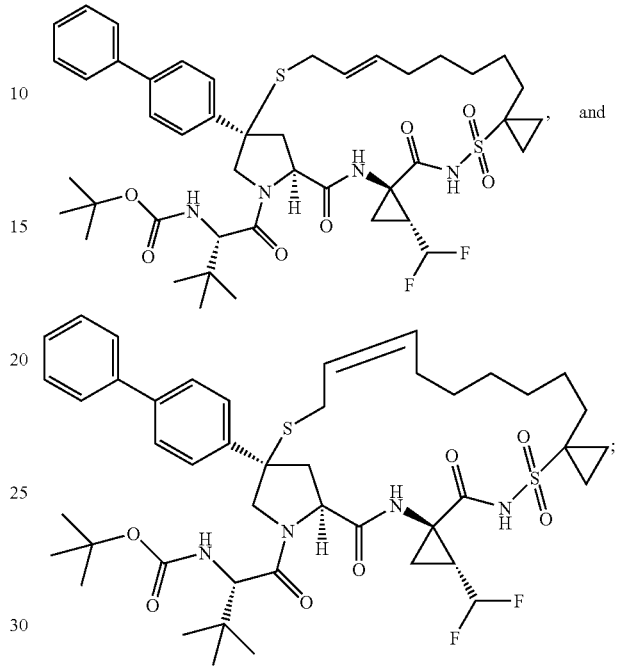

or
a pharmaceutically acceptable salt thereof.

9. A composition comprising the compound of claim 1, or a pharmaceutically acceptable salt thereof, and a pharmaceutically acceptable carrier.

10. The composition of claim 9 further comprising at least one additional compound having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, consensus interferon, interferon alpha 2A, and lymphoblastiod interferon tau.

13. The composition of claim 10 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, comprising administering to the patient a therapeutically effective amount of a compound of claim 1, or a pharmaceutically acceptable salt thereof.

16. The method of claim 15 further comprising administering at least one additional compounds having anti-HCV activity prior to, after, or simultaneously with the compound of claim 1, or a pharmaceutically acceptable salt thereof.

17. The method of claim 16 wherein at least one of the additional compounds is an interferon or a ribavirin.

18. The method of claim 17 wherein the interferon is selected from interferon alpha 2B, pegylated interferon alpha, consensus interferon, interferon alpha 2A, and lymphoblastiod interferon tau.

19. The method of claim 16 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,283,310 B2  
APPLICATION NO. : 12/635144  
DATED : October 9, 2012  
INVENTOR(S) : Alan Wang and Paul Scola Page 1 of 1

It is certified that error appears in the above-identified patent and that said Letters Patent is hereby corrected as shown below:

In the Claims:

Claim 12, col. 32, lines 45-46, delete "lymphoblastiod" and insert -- lymphoblastoid --, therefor.

Claim 13, col. 32, lines 51-52, delete "monophospate" and insert -- monophosphate --, therefor.

Claim 18, col. 33, lines 5-6, delete "lymphoblastiod" and insert -- lymphoblastoid --, therefor.

Claim 19, col. 34, lines 1-2, delete "monophospate" and insert -- monophosphate --, therefor.

Signed and Sealed this
Twenty-first Day of October, 2014

Michelle K. Lee
*Deputy Director of the United States Patent and Trademark Office*